United States Patent [19]

Leichter et al.

[11] 4,367,274

[45] Jan. 4, 1983

[54] SENSITIZED ORGANIC ELECTRON DONOR BIS-BENZOCARBAZOLE COMPOUNDS

[75] Inventors: Louis M. Leichter; Terry J. Sonnonstine; John J. Stofko, Jr., all of Saint Paul, Minn.

[73] Assignee: Minnesota Mining and Manufacturing Company, St. Paul, Minn.

[21] Appl. No.: 236,892

[22] Filed: Feb. 23, 1981

[51] Int. Cl.$^3$ .............................................. G03G 5/06
[52] U.S. Cl. ........................................ 430/58; 430/59; 430/78; 430/81; 430/82; 430/80
[58] Field of Search .................. 430/59, 78, 83, 81, 430/82, 79, 58

[56] References Cited

U.S. PATENT DOCUMENTS 4,134,764  1/1979  Hoffman et al. ...................... 430/82

OTHER PUBLICATIONS

Hayashi et al., Bull. Chem. Soc. Japan, vol. 39, (1966), pp. 1670–1673.

*Primary Examiner*—John D. Welsh
*Attorney, Agent, or Firm*—Cruzan Alexander; Donald M. Sell; Mark A. Litman

[57] ABSTRACT

Electron donor compounds for use in electrophotographic constructions must be sensitized to desired regions of the electromagnetic spectrum. Novel bis-benzocarbazole derivatives which can be used as organic electron donor compounds have been found to be sensitized by polyquinoid and polyanthroquinoid dyes.

11 Claims, No Drawings

SENSITIZED ORGANIC ELECTRON DONOR BIS-BENZOCARBAZOLE COMPOUNDS

TECHNICAL FIELD

The present invention relates to novel photoconductive layers which comprise novel organic electron donor compounds and polyquinoid sensitizer dyes. These layers are particularly useful in imaging systems such as electrophotography or electroradiography.

BACKGROUND OF THE ART

The technology of electrophotography is commercially well established. A wide variety of processes and apparatus are used, although they have many characteristics in common. One of the more common forms of this technology involves the use of a plate having a photoconductive insulating layer, generally coated on a conductive layer. Imaging is effected by first uniformly electrostatically charging the surface of the photoconductive layer and then exposing the charged layer to an image or pattern of activating electromagnetic radiation, usually visible light or ultraviolet radiation. This exposure selectively enables the charge in the irradiated areas of the photoconductive insulator to dissipate. The charge which remains in the non-irradiated areas forms a latent image which may be further processed to form a more permanent record of the exposing image or pattern. The most common form of additional processing involves the attraction of particles of material selectively to the charged areas and fusing them to the photoconductive layer or transferring the particles in their imagewise distribution to another surface to which they are more permanently bound by an adhesive or by fusion of the particles themselves. A common electrophotographic construction comprises, in sequence, a substrate, a conductive layer, and photoconductive insulator.

Typical classes of photoconductive materials useful in electrophotography include (1) inorganic crystalline photoconductors such as cadmium sulfide, cadmium sulfoselenide, cadmium selenide, zinc sulfide, zinc oxide, and mixtures thereof, (2) inorganic photoconductive glasses such as amorphous selenium, selenium alloys, and selenium-arsenic, and (3) organic photoconductors such as phthalocyanine pigments and polyvinyl carbazole, with or without binders and additives which extend their range of spectral sensitivity. These systems are well known in the art. For example, U.S. Pat. No. 3,877,935 discusses various problems associated with the crystalline and amorphous classes of photoconductors and shows the use of polynuclear quinone pigments in a binder as a photoconductive layer. U.S. Pat. No. 3,824,099 shows the use of squaric acid methine sensitizing dyes and triaryl pyrazoline charge transport materials as an electrophotographic construction. Cadmium sulfoselenide plates are shown in U.S. Pat. No. 3,764,315, and one of the original disclosures of the use of poly-N-vinylcarbazole as a photoconductive insulating layer is provided in U.S. Pat. No. 3,037,861. A number of diverse organic photoconductors have been disclosed since the development of the carbazole class of photoconductors such as quinones and anthrones (e.g., Hayashi et al., *Bull. Chem. Soc. Japan*, vol. 39, (1966) pp. 1670-1673), but the carbazoles have continued to attract the greatest attention.

Problems particularly associated with the use of carbazoles as a positive charge transporting material which is capable of supporting the injection of photoexcited holes from a photoconductive layer and is capable of transporting the injected holes also exist in this area of technology. The carbazole condensates with aldehydes as shown in U.S. Pat. No. 4,025,341 have a tendency to oligomerize. This oligomerization can cause a number of problems. The oligomers formed are not of a uniform molecular weight and carbazole content. This creates problems in purification and can create undesirable variations in photoconductive or charge transport properties. Triaryl methanes including a carbazole moiety (as shown in Xerox Disclosure Journal, Vol 3, No. 1, Jan./Feb. 1978, page 7) also tend to be sensitive to oxidation which converts them to an ionic species which will not act as a photoconductive insulator.

Japanese Patent Publication No. 52-34735 discloses carbazole organic photoconductor materials which may have substituents thereon which would inherently prevent oligomerization of the carbazoles. This is not recognized in the disclosure and the carbazoles would still be subject to oxidation problems.

SUMMARY OF THE INVENTION

A novel class of electronically active organic donor compounds has the formula:

where X is

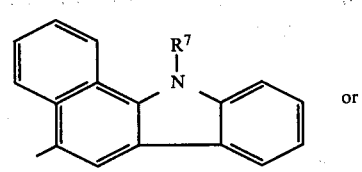

or

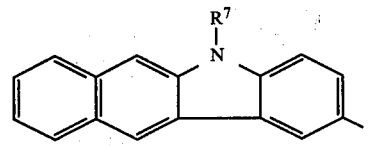

wherein R is an aliphatic, aromatic, or mixed aliphatic-aromatic group and Y is an aliphatic, aromatic or mixed aliphatic-aromatic group. For example, R and Y may be independently selected from alkyl groups, benzyl groups, phenyl groups, naphthyl groups, anthracyl groups, etc., with such various substituents as alkoxy groups, amine groups, alkyl groups, hydroxyl groups, and halogen atoms thereon.

These compounds have been found to be electron donor compounds and are useful in forming photoconductive layers when sensitized with polyquinoid dyes. They may be combined with polymeric binder materials to form photoconductive layers which are solid state molecular solution transport layers. The donor compounds have a reduced sensitivity to oxygen and oligomerization.

DETAILED DESCRIPTION OF THE INVENTION

The novel compounds of the present invention are bis(benzocarbazoles) which may be represented by the formula

wherein X is

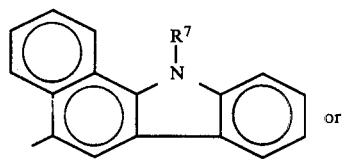

or

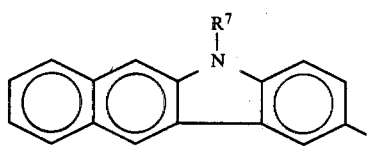

wherein

R⁷ is an aliphatic, aromatic or mixed aliphatic-aromatic group and

Y is an aliphatic, aromatic, heterocyclic, or mixed aliphatic-aromatic group.

All of the compounds of the present invention may be synthesized by reacting the appropriate N-substituted benzo[a]carbazole or benzo[b]carbazole:

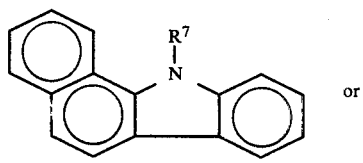

or

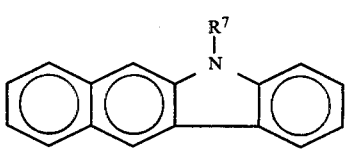

with the correspondingly appropriate aldehyde:

This process can be carried out in a solvent (e.g., ethanol) in the presence of an acid (e.g., HCl) catalyst. The reaction product may be isolated by simple filtration and washing. For example, in the reaction of N-ethyl-benzo[a]carbazole with benzaldehyde in ethanol in the presence of HCl as a catalyst, the preferential reaction of the aldehyde at the 5-position of the N-benzo[a]carbazole and the insolubility of the reaction product:

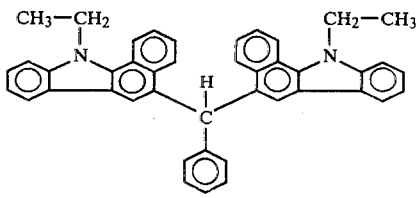

in ethanol, no oligomeric species are formed such as occur in a similar reaction with N-ethyl-carbazole. The reaction product is also stabilized against oxidation of the methine group by the rings ortho to point at which the methine group is bonded to the benzocarbazole nucleus.

$R^7$ may, as previously stated, be selected from aliphatic, aromatic and mixed aliphatic-aromatic groups. These groups may or may not be substituted. If they are substituted, it would be preferred that they be electron donating substituents although electron withdrawing substituents may be tolerated. Preferably $R^7$ is selected from alkyl groups of 1 to 20 carbon atoms, preferably n-alkyl groups of 2 to 20 carbon atoms, aryl groups such as phenyl or naphthyl groups, with phenyl groups preferred, alkaryl groups, for example benzyl groups, and allyl groups. Where the term 'group' is used anywhere in the practice of the present invention, as opposed to the term 'radical', the possibility of substitution is specifically intended to be included within the definition of that term. For example, n-alkyl radical may be only of the formula $-(CH_2)_n-CH_3$ while n-alkyl group may have hydrogen atoms on the n-alkyl radical substituted with other moieties such as halogen atoms, hydroxyl radicals, alkoxy radicals, alkyl radicals, amine radicals, cyano radicals, etc. Specific examples of useful $R^7$ moieties are ethyl, n-butyl, n-propyl, 4-methoxybutyl, 3-chloropropyl, 8-hydroxyoctyl, phenyl, benzyl, allyl, p-ethylphenyl, m-tert-butylnaphthyl, p-diethylaminophenyl, stearyl, dodecyl, etc. $R^7$ preferably has fewer than 20 carbon atoms, but may have up to 30 or more carbon atoms. The main influence of this group, except where electronic induction occurs because of a change of the nature of this group, is in the solubility of the compound.

Y may, as previously stated, be selected from aliphatic, aromatic, heterocyclic, and mixed aliphatic-aromatic groups. These groups may or may not be substituted. Examples of useful moieties are methyl, ethyl, n-pentyl, nonyl, stearyl, tolyl, anisyl (m-, p-, and o-), p-chlorobenzyl, o-bromobenzyl, p-hydroxybenzyl, veratryl, isobutyl, terphthalyl, p-octyloxybenzyl, p-dimethylaminophenyl, t-butyl, etc. Preferred Y moieties are phenyl, tolyl, anisyl, and benzyl groups because of their availability. As with group R, the main influence of this group, except with regard to electron induction effects, is on the solubility of the compounds. Preferably Y has 20 or fewer carbon atoms, but up to 30 may be readily tolerated. These novel compounds are disclosed in U.S. Ser. No. 237,068, filed in the name of John J. Stofko, Jr. et al. on the same date as this application.

The polyquinoid sensitizers which are a part of the present invention are disclosed in U.S. Pat. Nos. 4,134,764 and 4,205,005. These references teach polyquinoid dyes (including anthraquinoid dyes) in photoconductive binders as sensitizer dyes.

The dyes may be represented by the formulae:

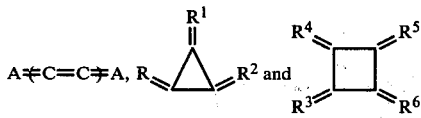

wherein

A is selected from quinoid and anthraquinoid groups,

R and R¹ are selected from quinoid and anthraquinoid groups,

R² is selected from quinoid group, anthraquinoid group, and an oxygen atom,

R³ is a quinoid group, and

R⁴, R⁵ and R⁶ are selected from the class consisting of quinoid groups and oxygen atoms with the priviso that at least one of R⁴, R⁵ and R⁶ must be a quinoid group.

The term quinoid group refers to a quinoid ring, i.e.:

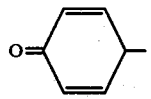

These quinoid groups may bear substituents which should be no more electron withdrawing than chlorine in positions ortho to the quinoid carbonyl group. That is, referring to the following formula, substituents $X_1$ and $X_2$ may be independently positioned only as shown below:

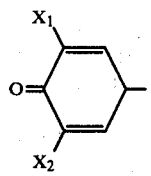

wherein $X_1$ and $X_2$ are groups no more electron withdrawing than chlorine.

One or two substituents may be present in place of hydrogen atoms. Such substituents may include, for example, alkyl and alkoxy groups (straight or branched, preferably having from 1 to 20 carbon atoms), phenyl, phenoxy, halophenyl, alkyl and alkoxy substituted phenyl (having 1 to 10 carbon atoms on the substituent groups), amino, iodo, bromo, chloro, carboxyl, carbanyl, and amido groups.

Various binder materials known in the art are useful with the electronically active donor compounds of the present invention. It is of course preferred that the binder be essentially optically transparent or at least transparent to the wavelengths of radiation to which the compounds (sensitized or not) are sensitive. Amongst the useful binders are poly(vinyl chloride), poly(siloxanes), poly(vinyl butyral), poly(vinyl acetate), styrene/acrylonitrile copolymers, polyacrylates, polymethacrylates, polycarbonates, polyepoxides, polyurethanes, polyamides, polyethers, polyesters, polyolefins as well as block, graft, random, and alternating polymers, copolymers, terpolymers and mixtures thereof and the like. The binders are preferably electrically inactive themselves. The preferred polymeric binders are polycarbonates, polyesters, and styrene/acrylonitrile copolymers. Coating aids, lubricants, surface active agents, and other adjuvants may be added to the composition.

For use of the materials of the present invention as electrophotographic layers, the organic electron donor compounds should be present as at least 20 percent by weight of the composition. Preferably the donor compound should be present as at least 25 or 35 percent by weight of the layer, and may comprise up to 100 percent by weight of the layer, excluding, of course, the sensitizer dye. The sensitizing dyes should be used in amounts which will increase the sensitivity of the composition. This is defined as an effective sensitizing amount of dye. Ordinarily amounts of up to 10 percent by weight dye may be used, but certain constructions can be envisaged with as much as 90 percent by weight of dye and 10 percent by weight of organic electron donor compounds. Amounts of dye as small as 0.005 percent by weight can be useful. More preferred concentration ranges are between 0.05 and 5 percent by weight.

The photosensitive materials of the present invention may also be useful as photoconductive toners, photovoltaic devices, organic semiconductors, and the like, and may use concentrations of organic electron donor compounds as low as 5 percent by weight.

It has been surprisingly noted that the benzocarbazole-aldehyde condensation products of the present invention are better charge transport materials than the corresponding benzocarbazoles by themselves. This is surprising because it is the benzocarbazole nucleus which is the electrically active portion of both molecules. Even when benzocabazoles were used in reasonably higher molecular proportions to the binder than were the condensates, the condensates would still perform better.

These and other aspects of the present invention will be shown in the following examples.

EXAMPLE 1

Synthesis of bis-5,5'-(N-ethylbenzo[a]carbazolyl)phenylmethane

Into a round bottom flask equipped with a reflux condenser and a mechanical stirrer were added 22.4 grams (0.1 mole) of N-ethylbenzo[a]carbazole and 5.3 grams (0.05 mole) of benzaldehyde. Two hundred milliliters of ethanol acidified with 8 ml of concentrated hydrochloric acid were then added. The mixture was stirred at reflux under a nitrogen atmosphere for sixteen hours. The insoluble, pure white product was isolated by filtration, washed with 100 ml of ethanol, and dried in a vacuum oven. The yield was 95% of the theoretic calculation.

EXAMPLES 2-17

In a manner substantially identical to that of the previous example, electronically active electron donor compounds of the present invention were obtained by condensing N-ethylbenzo[a]carbazole with each of the following aldehydes in equimolar replacement for the benzaldehyde:

2. p-tolualdehyde
3. m-tolualdehyde
4. o-tolualdehyde
5. p-anisaldehyde
6. m-anisaldehyde
7. o-anisaldehyde
8. p-chlorobenzaldehyde 9. p-bromobenzaldehyde
10. o-bromobenzaldehyde
11. p-hydroxybenzaldehyde
12. α-naphthaldehyde
13. veratraldehyde
14. p-octyloxybenzaldehyde
15. iso-butyraldehyde
16. n-nonylaldehyde
17. terphthaldehyde

EXAMPLES 18-21

In a manner substantially identical to that of Example 1, the following combinations of carbazoles and aldehydes were used to synthesize compounds of the present invention.
18. benzo[a]carbazole and benzaldehyde
19. N-ethylbenzo[b]carbazole and benzaldehyde
20. N-ethyldibenzo[a,g]carbazole and benzaldehyde
21. N-ethyl-8-methoxybenzo[a]carbazole and benzaldehyde The addition of any of the compounds produced in Examples 1-21 to electrically inert polymeric binders formed positive charge transport layers. These layers could be formed on photoconductive layers and were capable of supporting injected photogenerated holes from the photoconductive layer and allowed the transport of these holes through the transport layer to selectively discharge the surface charge.

EXAMPLE 22

A bulk sensitized photoreceptor was prepared by coating a solution consisting of 15 percent by weight solids (5.2% diquinoanthraquinocyclopropane, 47.4% by weight of the compound prepared in Example 1, and 47.4% of a polycarbonate resin) were coated at about $1 \times 10^{-4}$m wet thickness onto an aluminum vapor coated poyethyleneterephthalate film. The sample was air dried at 85° C. for 15 minutes. The photoreceptor charged to 720 volts under positive corona charging and the charge was reduced to about 360 volts with little dark decay by an exposure of 0.54 foot-candle-seconds to a tungsten lamp. The device was also found to display high charge acceptance, low dark decay, and negligible fatigue upon cycling.

EXAMPLE 23

A bilayer photoreceptor was prepared by overcoating a solution of triquinocyclopropane and polyvinylbutyral (50/50) as a 15 percent by weight solution in 1,2-dichloroethane onto an aluminized polyester film coated with a fifty/fifty percent solid solution of bis(N-ethyl-1,2-benzocarbozolyl)phenyl methane and polycarbonate resin. The sample was air dried overnight at room temperature. The device displayed high charge acceptance, low dark decay, negligible fatigue on cycling, and the ability to discharge completely.

I claim:
1. A spectrally sensitized electrically active donor compound of the formula

where X is

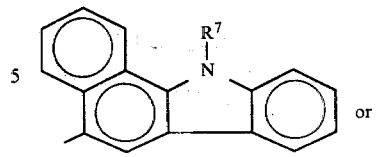

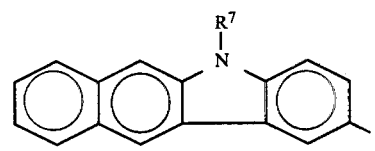

wherein $R^7$ and Y are independently selected from the group consisting of aliphatic, aromatic, heterocyclic, and mixed aliphatic-aromatic groups, sensitized by an effective amount of a polyquinoid dye selected from the class consisting of:

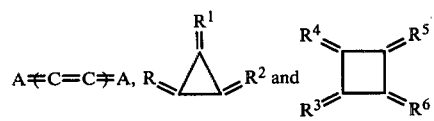

wherein
A is selected from quinoid and anthraquinoid groups,
R and $R^1$ are selected from quinoid and anthraquinoid groups,
$R^2$ is selected from quinoid groups, anthraquinoid groups, and an oxygen atom,
$R^3$ is a quinoid group, and
$R^4$, $R^5$ and $R^6$ are selected from the class consisting of quinoid groups and oxygen atoms with the proviso that at least one of $R^4$, $R^5$ and $R^6$ must be a quinoid group.
2. The compound of claim 1 wherein Y is an aromatic group.
3. The compound of claim 1 wherein $R^7$ is an alkyl group of from 1 to 20 carbon atoms.
4. The compound of claim 1 wherein Y is an aromatic group, $R^7$ is selected from the group consisting of an alkyl group of 2 to 20 carbon atoms, phenyl group, naphthyl group, or benzyl group, and the polyquinoid dye is a cyclopropane or cyclobutane polyquinoid dye.
5. The compound of claim 1 wherein Y is phenyl and $R^7$ is n-alkyl of 2 to 20 carbon atoms.
6. An electrically active photoconductive insulating layer comprising a polymeric binder and the spectrally sensitized compound of claim 1.
7. An electrically active photoconductive insulating layer comprising a polymeric binder and the spectrally sensitized compound of claim 4.
8. The layer of claim 6 wherein Y is an aromatic group.
9. The layer of claims 6, 7, or 8 wherein $R^7$ is an alkyl group of 2 to 20 carbon atoms, phenyl group, naphthyl group or benzyl group.
10. The layer of claims 6 or 8 wherein Y is phenyl and $R^7$ is n-alkyl of 2 to 20 carbon atoms.
11. An electrophotographic element comprising, in sequence, a conductive layer, a charge generating layer, and the photoconductive insulating layer of claims 6, 7, or 8.

* * * * *